United States Patent [19]

Gotoh et al.

[11] Patent Number: 4,929,753

[45] Date of Patent: May 29, 1990

[54] PREPARATION OF TRIFLUOROMETHYLBENZOIC ACID FROM HEXAFLUOROXYLENE

[75] Inventors: Yoshihiko Gotoh, Kamifukuoka; Toshikazu Kawai, Kawagoe, both of Japan

[73] Assignee: Central Glass Company, Limited, Ube, Japan

[21] Appl. No.: 183,243

[22] Filed: Apr. 19, 1988

[30] Foreign Application Priority Data

Apr. 22, 1987 [JP] Japan ................................. 62-97288

[51] Int. Cl.$^5$ ........................................... C07C 51/16
[52] U.S. Cl. ..................................... 562/411; 562/422
[58] Field of Search ................................ 562/422, 411

[56] References Cited

U.S. PATENT DOCUMENTS 3,792,048  2/1974  Hansl ................................... 562/422

OTHER PUBLICATIONS

"Some Reactions of the Trifloromethyl Group in the Benzotrifluoride Series. I. Hydrolysis", J. Am. Chem. Soc., vol. 41, pp. 4148–4149 (1949).

Saul Patai, The Chemistry of Acid Derivatives (Part 1), pp. 275–276 (1979).

*Primary Examiner*—Paul J. Killos
*Attorney, Agent, or Firm*—Fleit, Jacobson, Cohn, Price, Holman & Stern

[57] ABSTRACT

Trifluoromethylbenzoic acid is obtained at high yield from $\alpha,\alpha,\alpha,\alpha',\alpha',\alpha'$-hexafluoroxylene, which is a relatively inexpensive compound, by reacting this compound with a strong acid in sulfuric acid which is at least partly fuming sulfuric acid. It is best to use fuming sulfuric acid as the strong acid. The reaction temperature ranges from room temperature to 150° C., though temperatures below 100° C. are preferable. By this reaction only one trifluoromethyl group of hexafluoroxylene is hydrolyzed so far as the strong acid is not in large excess.

9 Claims, No Drawings

PREPARATION OF TRIFLUOROMETHYLBENZOIC ACID FROM HEXAFLUOROXYLENE

BACKGROUND OF THE INVENTION

This invention relates to a novel method for preparing trifluoromethylbenzoic acid, a compound useful as an intermediate material for medicines, agricultural chemicals, liquid crystals, etc.

It is known to synthesize trifluoromethylbenzoic acid from a benzotrifluoride derivative. For example, p-trifluoromethylbenzoic acid can be prepared from p-trifluoromethylbenzaldehyde by Cannizzaro reaction, from p-trifluoromethylbenzoyl chloride by alkali hydrolysis and from p-trifluoromethylbenzal chloride by acid hydrolysis. However, no one of these known methods can provide trifluoromethylbenzoic acid at low price because of using a costly compound as the starting material.

SUMMARY OF THE INVENTION

It is an object of the present invention to provide a novel method for economically preparing trifluoromethylbenzoic acid.

According to the invention, trifluoromethylbenzoic acid is prepared from $\alpha,\alpha,\alpha,\alpha',\alpha',\alpha'$-hexafluoroxylene by reacting this compound with a strong acid in sulfuric acid at least a portion of which is fuming sulfuric acid to thereby hydrolyze one trifluormethyl group of the starting compound.

$\alpha, \alpha, \alpha, \alpha', \alpha', \alpha'$-Hexafluoroxylene is a relatively inexpensive material, and we have discovered that only one of the two trifluoromethyl groups of this compound can selectively be hydrolyzed by the above stated reaction.

The method according to the invention can provide trifluoromethylbenzoic acid at a greatly reduced price by virtue of inexpensiveness of the starting material, simplicity of the reaction operation and high yield of the desired reaction product. As a matter of course p-trifluoromethylbenzoic acid is obtained from $\alpha, \alpha, \alpha,\alpha', \alpha', \alpha'$-hexafluoro-p-xylene and m-trifluoromethylbenzoic acid from $\alpha, \alpha, \alpha, \alpha', \alpha', \alpha'$-hexafluoro-m-xylene, and there is little difference between the two cases in the acid hydrolysis reaction itself.

DESCRIPTION OF THE PREFERRED EMBODIMENTS

In carrying out the acid hydrolysis reaction according to the invention, existence of free water in the reaction system is detrimental and should be prevented. Therefore, it is preferred to carry out the reaction in fuming sulfuric acid. When concentrated sulfuric acid is used, fuming sulfuric acid should be added.

As a strong acid for hydrolyzing one trifluoromethyl group of $\alpha, \alpha, \alpha, \alpha', \alpha', \alpha',$-hexafluoroxylene, it is desirable to use fuming sulfuric acid, sulfur trioxide (sulfuric acid anhydride), fluorosulfuric acid, trifluoromethane sulfonic acid or a Lewis acid such as aluminum chloride or antimony pentachloride. If desired, two or more kinds of strong acids may be used jointly. It is suitable that the quantity of the strong acid used for the reaction is approximately equivalent to the trifluoromethyl group to be hydrolyzed. Use of a largely excessive amount of strong acid results in formation of a large quantity of phthalic acid by hydrolysis of both trifluoromethyl groups of the starting compound. In the case of using antimony pentachloride as the strong acid it suffices that antimony pentachloride amounts to about 10 mol % of the trifluoromethyl group to be hydrolyzed because this Lewis acid acts catalytically.

As the reaction medium, it is necessary to use at least 2 mols of sulfuric acid per mol of the above described strong acid. The reaction temperature may range from room temperature to about 150° C. Although it is possible to make the reaction at a relatively high temperature by using a relatively small quantity of a strong acid, it is better to carry out the reaction at a temperature not higher than 100° C. by using a sufficient quantity of a strong acid, preferably fuming sulfuric acid. For industrial practice of the invention it is most favorable to carry out the reaction at about 50°–60 C. for several hours by using such a quantity of fuming sulfuric acid as is approximately equivalent to the trifluoromethyl group to be hydrolyzed. For example, by reacting $\alpha, \alpha, \alpha, \alpha', \alpha', \alpha'$-hexafluoro-p-xylene with such an appropriate quantity of fuming sulfuric acid at about 55° C. for about 6 hr, p-trifluoromethylbenzoic acid of 97–99% purity is obtained.

On condition that the quantity of the strong acid and the reaction temperature are controlled appropriately as described above, the hydrolyzing reaction of one trifluoromethyl group of the starting compound is not followed by substantial hydrolysis of the other trifluoromethyl group even though the trifluoromethylbenzoic acid formed by the reaction is kept under the same reaction conditions.

The reason for the selective hydrolysis of only one of the two trifluoromethyl groups of the starting compound has not fully been elucidated yet. Presumably, once either of the two trifluoromethyl groups is hydrolyzed the remaining one becomes resistant to the attack by the strong acid under the same reaction conditions.

The invention is further illustrated by the following nonlimitative examples.

EXAMPLE 1

In a three-necked glass flask having a capacity of 500 ml, 200 g of $\alpha, \alpha, \alpha, \alpha', \alpha', \alpha'$-hexafluoro-p-xylene was heated to 55° C. Then 249.2 g of 30% fuming sulfuric acid was slowly dropped into the flask, and stirring was continued for 6 hr under the same temperature condition. After that the reaction liquid was cooled and poured into 1.5 kg of iced water, which caused precipitation of a crystalline substance. The precipitate was collected by filtration and was washed and dried to thereby obtain 159.4 g of crude crystals of p-trifluoromethylbenzoic acid. The purity of this product was 97.5%, and the remaining part was phthalic acid.

Analysis of the product gave the following results.
Melting point: sublimed. $^1$H-NMR (in acetone (D-6), standard was TMS):
$\delta$7.76–7.98 (m, 2H), 8.12–8.32 (m, 2H), 10.30 (b, 1H).
$^{19}$F-NMR (in acetone (D-6), standard was CFCl$_3$): 62.59 ppm (s).
Infrared Absorption (KBr pellet): 3100 cm$^{-1}$ (O-H), 1710 cm$^{-1}$ (C=O).

EXAMPLE 2

A 30-ml reactor made of glass was charged first with 5 g of $\alpha,\alpha,\alpha,\alpha', \alpha', \alpha'$-hexafluoro-m-xylene and further with 6.5 g of 30% fuming sulfuric acid, and the mixture was heated to 50° C. and stirred for 4 hr. After that the reaction liquid was cooled and poured into 50 g of iced water, which caused precipitation of a crystalline substance. The precipitate was collected by filtration and was washed and dried to thereby obtain 3.1 g of crude crystals of m-trifluoromethylbenzoic acid. The purity of this product was 97.4%, and the remaining part was phthalic acid.

Analysis of the product gave the following results. Melting point: 103°–104° C. $^1$H-NMR (in acetone (D-6), standard was TMS): $\delta$8.60–9.08 (m, 2H), 9.16–9.40 (m, 2H), 9.70 (b, 1H).

$^{19}$F-NMR (in acetone (D-6), standard was CFCl$_3$): 62.35 ppm (s).

Infrared Absorption (KBr pellet): 3100 cm$^{-1}$ (O-H), 1700 cm (C=O).

EXAMPLE 3

A mixture of 5 g of 97% sulfuric acid and 2.2 g of 30% fuming sulfuric acid was added to 5 g of $\alpha, \alpha, \alpha, \alpha', \alpha', \alpha'$-hexafluoro-p-xylene and, furthermore, 0.7 g of antimony pentachloride was added. The resultant mixture was heated to 50° C. and stirred for 5.5 hr. After that the reaction liquid was poured into 50 g of iced water, and a crystalline precipitate was collected by filtration and was washed and dried to thereby obtain 3.9 g of crude crystals of p-trifluoromethylbenzoic acid. The purity of this product was 92.1%, and the remaining part was phthalic acid.

EXAMPLE 4

A mixture of 3 g of 97% sulfuric acid and 1.3 g of 30% fuming sulfuric acid and 4.2 g of fluorosulfuric acid was added to 3 g of $\alpha, \alpha, \alpha, \alpha', \alpha', \alpha'$-hexafluoro-p-xylene, and the resultant mixture was heated to 70° C. and stirred for 1.5 hr. After that the reaction liquid was poured into 50 g of iced water, and a crystalline precipitate was collected by filtration and was washed and dried to thereby obtain 2.69 g of crude crystals of p-trifluoromethylbenzoic acid. The purity of this product was 97.0%, and the remaining part was phthalic acid.

What is claimed is:

1. A method of preparing trifluoromethylbenzoic acid, comprising the step of reacting $\alpha, \alpha, \alpha, \alpha', \alpha', \alpha'$-hexafluoroxylene with a strong acid in sulfuric acid at least a portion of which is fuming sulfuric acid to thereby hydrolyze one trifluoromethyl group of said hexafluoroxylene.

2. A method according to claim 1, wherein said strong acid comprises at least one acid selected from the group consisting of fuming sulfuric acid, sulfuric acid anhydride, fluorosulfuric acid, trifluoromethane sulfonic acid, antimony pentachloride and aluminum chloride.

3. A method according to claim 1, wherein the reaction is carried out at a temperature in the range from room temperature to about 150° C.

4. A method according to claim 3, wherein said temperature is not higher than 100° C.

5. A method according to claim 4, wherein said strong acid is fuming sulfuric acid.

6. A method according to claim 1, wherein the quantity of said strong acid is approximately equivalent to one trifluoromethyl group of said hexafluoroxylene.

7. A method according to claim 1, wherein the quantity of said sulfuric acid is at least twice the quantity of said strong acid by mol.

8. A method according to claim 1, wherein said hexafluoroxylene is $\alpha, \alpha, \alpha, \alpha', \alpha', \alpha'$-hexafluoro-p-xylene.

9. A method accoridng to claim 1, wherein said hexafluoroxylene is $\alpha, \alpha, \alpha, \alpha', \alpha', \alpha'$-hexafluoro-m-xylene.

* * * * *